United States Patent
Que et al.

(10) Patent No.: US 9,486,223 B2
(45) Date of Patent: Nov. 8, 2016

(54) MECHANICALLY DATACHABLE VASO-OCCLUSIVE DEVICE

(71) Applicant: Boston Scientific Scimed, Inc., Maple Grove, MN (US)

(72) Inventors: Like Que, Livermore, CA (US); Esther Chang, Fremont, CA (US); Ann Huang, Fremont, CA (US); Thazin Win, Chicago, IL (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 14/589,642

(22) Filed: Jan. 5, 2015

(65) Prior Publication Data

US 2015/0119924 A1 Apr. 30, 2015

Related U.S. Application Data (63) Continuation of application No. 11/942,890, filed on Nov. 20, 2007, now Pat. No. 8,926,650.

(60) Provisional application No. 60/866,593, filed on Nov. 20, 2006.

(51) Int. Cl.
*A61B 17/12* (2006.01)
*A61B 17/00* (2006.01)

(52) U.S. Cl.
CPC ... *A61B 17/12145* (2013.01); *A61B 17/12022* (2013.01); *A61B 17/12113* (2013.01); *A61B 2017/00477* (2013.01); *A61B 2017/12054* (2013.01)

(58) Field of Classification Search
CPC .............. A61B 17/12022; A61B 17/12113; A61B 17/12145; A61B 2017/00477; A61B 2017/12054
See application file for complete search history.

(56) References Cited

U.S. PATENT DOCUMENTS

| | | | | |
|---|---|---|---|---|
| 5,925,059 A | * | 7/1999 | Palermo | A61B 17/12022 606/191 |
| 7,367,987 B2 | * | 5/2008 | Balgobin | A61B 17/12022 606/191 |
| 7,371,251 B2 | * | 5/2008 | Mitelberg | A61B 17/12022 606/191 |
| 8,257,422 B2 | * | 9/2012 | Schaeffer | A61M 25/01 623/1.11 |
| 2004/0199175 A1 | * | 10/2004 | Jaeger | A61B 17/12022 606/108 |
| 2006/0025801 A1 | * | 2/2006 | Lulo | A61B 17/12022 606/200 |
| 2006/0025802 A1 | * | 2/2006 | Sowers | A61B 17/12022 606/200 |
| 2006/0116714 A1 | * | 6/2006 | Sepetka | A61B 17/12022 606/200 |
| 2006/0276834 A1 | * | 12/2006 | Balgobin | A61B 17/12022 606/200 |
| 2007/0021775 A1 | * | 1/2007 | Vrba | A61M 25/09 606/200 |
| 2007/0055302 A1 | * | 3/2007 | Henry | A61B 17/12022 606/200 |
| 2007/0179520 A1 | * | 8/2007 | West | A61B 17/12022 606/200 |

* cited by examiner

*Primary Examiner* — Julie A Szpira (57) ABSTRACT

A device for delivering an occlusive element includes an elongate pusher member having a lumen extending between distal and proximal ends. An elongate releasing member is slideably disposed within the lumen of the elongate pusher member. A retaining member is disposed on the distal end of the elongate pusher member and includes a finger portion having an aperture sized to receive the distal end of the elongate releasing member. An occlusive element such as a coil is provided and includes a securing member positioned at a proximal end thereof. The securing member is releaseably secured to the finger portion of the retaining member. The securing member is secured to the finger portion when the elongate releasing member is disposed in the aperture of the finger portion and unsecured when the elongate releasing member is retracted proximally from the aperture of the finger portion.

16 Claims, 5 Drawing Sheets

MECHANICALLY DATACHABLE VASO-OCCLUSIVE DEVICE

CROSS REFERENCE TO RELATED APPLICATIONS

This application is a Continuation of U.S. patent application Ser. No. 11/942,890, filed Nov. 20, 2007, which claims the benefit under 35 U.S.C. §119 to U.S. provisional patent application Ser. No. 60/866,593, filed Nov. 20, 2006. The foregoing application is hereby incorporated by reference into the present application in its entirety.

FIELD OF THE INVENTION

The field of the invention generally relates to systems and delivery devices for implanting vaso-occlusive devices for establishing an embolus or vascular occlusion in a vessel of a human or veterinary patient.

BACKGROUND OF THE INVENTION

Vaso-occlusive devices or implants are used for a wide variety of reasons, including treatment of intra-vascular aneurysms. A common vaso-occlusive device takes the form of a soft, helically wound coil formed by winding a platinum (or platinum alloy) wire strand about a primary mandrel. The relative stiffness of the coil will depend, among other things, on its composition, the diameter of the wire strand, the diameter of the primary mandrel, and the pitch of the primary windings. The coil is then wrapped around a larger, secondary mandrel, and again heat treated to impart a secondary shape. For example, U.S. Pat. No. 4,994,069, issued to Ritchart et al., describes a vaso-occlusive coil that assumes a linear, helical primary shape when stretched for placement through the lumen of a delivery catheter, and a folded, convoluted secondary shape when released from the delivery catheter and deposited in the vasculature.

In order to deliver the vaso-occlusive coils to a desired site, e.g., an aneurysm, in the vasculature, it is well-known to first position a small profile, micro-catheter at the site using a steerable guidewire. Typically, the distal end of the micro-catheter is provided, either by the attending physician or by the manufacturer, with a selected pre-shaped bend, e.g., 45°, 90°, "J", "S", or other bending shape, depending on the particular anatomy of the patient, so that it will stay in a desired position for releasing one or more vaso-occlusive coil(s) into the aneurysm once the guidewire is withdrawn. A delivery or "pusher" wire is then passed through the micro-catheter, until a vaso-occlusive coil coupled to a distal end of the pusher wire is extended out of the distal end opening of the micro-catheter and into the aneurysm. The vaso-occlusive device is then released or "detached" from the end pusher wire, and the pusher wire is withdrawn back through the catheter. Depending on the particular needs of the patient, another occlusive device may then be pushed through the catheter and released at the same site.

One known way to release a vaso-occlusive coil from the end of the pusher wire is through the use of an electrolytically severable junction, which is a small exposed section or detachment zone located along a distal end portion of the pusher wire. The detachment zone is typically made of stainless steel and is located just proximal of the vaso-occlusive device. An electrolytically severable junction is susceptible to electrolysis and disintegrates when the pusher wire is electrically charged in the presence of an ionic solution, such as blood or other bodily fluids. Thus, once the detachment zone exits out of the catheter distal end and is exposed in the vessel blood pool of the patient, a current applied to the conductive pusher wire completes a circuit with an electrode attached to the patient's skin, or with a conductive needle inserted through the skin at a remote site, and the detachment zone disintegrates due to electrolysis.

U.S. Pat. No. 5,122,136 issued to Guglielmi, et al. discloses a device in which a portion of the guidewire connected between the tip and the body of the pusher wire is composed of stainless steel and exposed to the bloodstream so that upon continued application of a positive current to the exposed portion, the exposed portion is corroded away at least at one location and the tip is separated from the body of the guidewire. The guidewire and a microcatheter are thereafter removed leaving the guidewire tip embedded in the thrombus formed within the vascular cavity.

One perceived disadvantage with vaso-occlusive devices that are deployed using electrolytic detachment is that the electrolytic process requires a certain amount of time to elapse to effectuate release of the vaso-occlusive element. This time lag is also a perceived disadvantage for vaso-occlusive delivery devices that utilize thermal detachment mechanisms. U.S. Pat. No. 6,966,892 issued to Gandhi, et al. discloses a vaso-occlusive device that uses a thermal detachment system.

Another detachment modality used to deploy vaso-occlusive elements uses mechanical detachment. U.S. Pat. No. 5,800,453 issued to Gia discloses embolic coils that have a receiving slot on one end. A catheter control wire or pusher guidewire having a hook which engages the coil's receiving slot is used as a coil pusher to eject the coil at the chosen site. The coils may also be placed within the lumen with a catheter in a nose-to-tail fashion and pushed into the body lumen. Pushing the coil assembly via the pusher from the distal end of the catheter body uncouples the distal most coil.

Another example of a mechanical detachment system is disclosed in U.S. Pat. No. 5,800,455 issued to Palermo et al. Palermo et al. discloses a delivery system that includes a coil having a clasp or hook located at one end. The clasp or hook includes a passageway for a control wire. The clasp interlocks with another clasp located on a distal end of a pusher member. The control wire is withdrawn in the proximal direction to release the coil.

Still other mechanical detachments systems have been proposed that use a fiber segment that is pulled in the proximal direction to decoupled the fiber from the embolic coil device. Examples of these systems may be found in U.S. Patent Application Publication Nos. 2006/0025803 A1 (coiled fiber), 2006/0025802 A1 (U-shaped fiber), and 2006/0025801 A1 (detachment filament).

One problem with certain existing mechanical detachment systems is that the junction between the embolic element and the releasing member moves during the detachment process which may adversely impact the placement of the embolic element within the aneurysm. Another complication is that mechanical detachment systems tend to have a stiff main section that complicates accurate placement of the delivery system at the desired location. Mechanical detachment systems also are perceived by physicians as being harder to use than other devices. In addition, certain mechanical detachment systems may jeopardize the integrity of the embolic element (e.g. coil) after detachment.

There thus is a need for a vaso-occlusive delivery system that utilizes mechanical detachment yet does not suffer from the aforementioned deficiencies. Such a system should be easy to use yet provide for consistent detachment of embolic elements in the desired location. Moreover, the delivery system should be able to release the embolic element without extensive movement resulting from the detachment operation.

SUMMARY

In one embodiment, a device for delivering an occlusive element includes an elongate pusher member having a distal end and a proximal end and a lumen extending between the distal and proximal ends. An elongate releasing member having a distal end and a proximal end is slideably disposed within the lumen of the elongate pusher member. A retaining member is disposed on, or formed integrally or a continuation of, the distal end of the elongate pusher member, the retaining member having a finger portion having an aperture sized to receive the distal end of the elongate releasing member. The finger portion may also be integrated directly into the distal end of the elongate pusher member. An occlusive element including a securing member is positioned at a proximal end thereof. The securing member at the proximal end of the occlusion element or coil is releaseably secured to the finger portion of the retaining member. For example, the finger is inserted into the securing member which may be formed as a loop, hoop, or the like. The securing member is secured (e.g., locked) to the finger portion when the elongate releasing member is disposed in the aperture of the finger portion and unsecured (e.g., unlocked) when the elongate releasing member is retracted proximally from the aperture of the finger portion.

In one aspect, an optional stop is located on the finger portion of the retaining member. The stop limits movement of the elongate releasing member through the aperture in the distal direction. The finger portion may include an angular surface with an optional lubricious or low-friction coating.

In another aspect, a biasing member is provided on the retaining member. The biasing member may be located within a recess of the retaining member. The biasing member may be formed as a wire or spring that aids in releasing the coil from the retaining member.

In another embodiment of the invention, a device for delivering an occlusive element includes an elongate pusher member having a distal end and a proximal end and a lumen extending between the distal and proximal ends. To improve the flexibility of the distal end of the delivery device, a coil member is secured to the distal end of the elongate pusher member. A stretch resistant member such as a tubular braid or the like is positioned about the periphery of the coil member and is secured to the distal end of the pusher member. An elongate releasing member having a distal end and a proximal end is slideably disposed within the lumen of the elongate pusher member. A retaining member is disposed on the distal end of the coil member. The retaining member includes a clasp portion having an aperture sized to receive the distal end of the elongate releasing member. The device further includes an occlusive element such as, for example, a vaso-occlusive coil having a securing member positioned at a proximal end of the vaso-occlusive coil. The securing member of the occlusive element is releaseably secured to the clasp portion of the retaining member wherein the securing member is secured to the clasp portion when the elongate releasing member is disposed in the aperture of the clasp portion and unsecured when the elongate releasing member is retracted proximally from the aperture of the clasp portion. The clasp may include a finger around which the securing member is releaseably fastened. The finger may have an angular surface with an optional lubricious or low-friction coating.

The device delivery device described immediately above may also include the optional stop as well as the biasing member to assist in coil deployment. The coil member interposed between the elongate pusher member and the retaining member advantageously provides an articulating junction to provides added flexibility to the delivery device.

In still another aspect of the invention, a method of deploying a vaso-occlusive coil includes loading a vaso-occlusive coil on a distal end of an elongate pusher member by inserting a finger of a retaining member into a securing member of the vaso-occlusive coil. The vaso-occlusive coil is secured to the elongate pusher member by advancing an elongate releasing member distally within the elongate pusher member so as to insert a distal end of the elongate releasing member into an aperture in the finger of the retaining member. During a clinical procedure, the vaso-occlusive coil is positioned adjacent to a deployment site such as, for instance, an aneurysm. The elongate releasing member is retracted proximally relative to the elongate pusher member so as to release the vaso-occlusive coil from the finger.

DETAILED DESCRIPTION OF THE ILLUSTRATED EMBODIMENTS

Figure 1A:
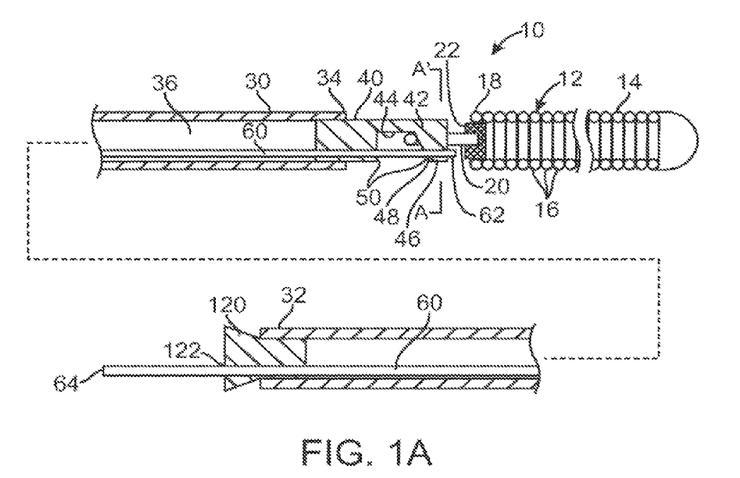
FIG. 1A is a cross-sectional view of a delivery device according to one embodiment.
Figure 5:
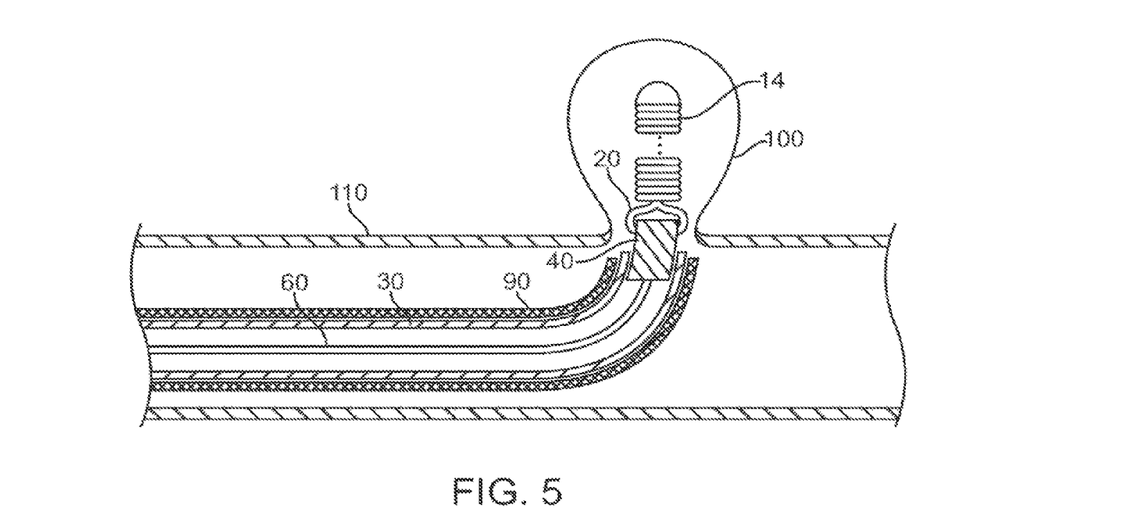
FIG. 5 is a partial cross-sectional view of a delivery device being positioned adjacent to a delivery site for deployment of a vaso-occlusive coil.

FIG. 1A illustrates a device 10 for delivering an occlusive element 12 to a vascular space such as, for example, aneurysm 100 (shown in FIG. 5). The occlusive element 12 may be formed as a vaso-occlusive coil 14 created from a plurality of coil windings 16. When manufacturing the vaso-occlusive coil 14, the coil material is wound into a coil shape, which will typically be linear. Generally speaking, the coil 14 is a metallic coil made from a platinum alloy or a super-elastic alloy such as titanium/nickel alloy, known as "NITINOL." The diameter of the wire used in the production of the coils 14 may fall in the range of about 0.00025 inches to about 0.006 inches. The coil 14 may have a primary diameter of between about 0.003 and about 0.025 inches, but for most neurovascular applications, a diameter between about 0.008 to about 0.018 inches provides sufficient hoop strength to hold the coil 14 in place within the chosen body site, lumen, or cavity, without substantially distending the wall of the site and without moving from the site as a result of the repetitive fluid pulsing found in the vascular system.

The axial length of the coil wire will usually fall in the range of around 0.5 to around 100 cm, more usually around 2.0 to 40 cm. Of course, all of the dimensions provided about should be viewed only as guidelines, and the invention, in its broader aspects, should not be limited thereto. Dimensions that are suitable for use in occluding sites within the human body are included in the scope of this invention.

Depending on the desired therapeutic effect and the shape of the site to be treated, the coil 14 may later be treated or accessorized in numerous ways in order to enhance its therapeutic effect. The coil 14 may be made to form various secondary shapes, often through the use of heat treatment, that may be better suited to fill a particular treatment site, as disclosed in U.S. Pat. Nos. 5,853,418 and 6,280,457, the entireties of which are expressly incorporated herein by reference. Alternatively, the coil 14 may have little or no shape after introduction into the vascular space, as disclosed in U.S. Pat. No. 5,690,666, the entirety of which is expressly incorporated by reference herein. In addition, external materials may be added to the outside of the coil 14 in an effort to increase its thrombolytic properties. These alternative embodiments are disclosed in U.S. Pat. Nos. 5,226,911, 5,304,194, 5,549, 624, 5,382,259, and 6,280,457, the entireties of which are expressly incorporated herein by reference.

As best seen in FIGS. 1A, 2A, 2B, and 4, the proximal end 18 of the coil 14 includes a securing member 20. The securing member 20 may be formed as a closed loop, hoop or ring as is illustrated in FIGS. 1A, 2A, 2B, 4, 6A, and 6B. Alternatively, the securing member 20 may be formed in an open configuration such as a hook or the like (not shown). The loop, hoop or ring form of the securing member 20 in FIGS. 1A, 2A, 2B, 4, 6A, and 6B has its two ends fixedly secured to a proximal end 18 of the coil 14. In one embodiment, the securing member 20 may be formed integrally with the coil 14. In this regard, the securing member 20 may be formed from a proximal winding of the coil 14. For example, the proximal winding may be looped back upon itself and optionally bonded to one or more windings 16 to form the closed securing member 20.

Alternatively, the securing member 20 may be formed separately from the coil 14. For example, the securing member 20 may be formed from a thin metal wire filament such as platinum, NITINOL, titanium, stainless steel, and metallic alloys. Alternatively, the securing member 20 may be formed using a polymer-based material such as NYLON, PTFE, polypropylene, polyimide, PEEK, and the like. The separate securing member 20 may then be jointed to the proximal end 18 of the coil 14 either by tying or through a bonding operation. For example, an adhesive material 22 (shown in FIGS. 1A and 4), solder, or a weld may be used to fixedly attach the securing member 20 to the proximal end 18 of the coil 14. If the securing member 20 is formed from a metallic material, the securing member 20 may be formed from a thin metal sheet using a photo-etching process. The liberated securing member 20 may then be jointed to the coil 14.

Figure 4:
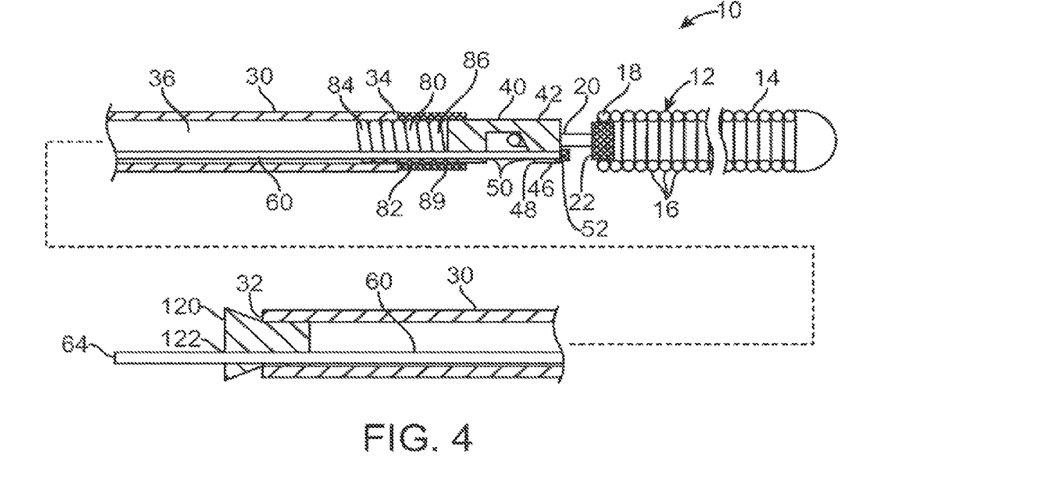
FIG. 4 is a cross-sectional view of a delivery device according to another embodiment. The delivery device includes a coiled member with an outer stretch resistant member.

Referring to FIG. 1A, the delivery device 10 includes an elongate pusher member 30 having a proximal end 32 and a distal end 34. A lumen 36 is formed within the elongate pusher member 30. The elongate pusher member 30 may be formed as a sheath or the like as is best shown in FIGS. 1A and 4. Alternatively, the elongate pusher member 30 may be formed at least in part by a coiled structure formed from a series of windings of material such as, for instance, metallic coil that is surrounded by a stretch resistant member 89 (illustrated in FIG. 4). In yet another alternative, at least a portion of the elongate pusher member 30 may be formed from a braided material to add flexibility. For example, a region near the distal end 34 of the elongate pusher member 30 may be formed from a coil and stretch resistant member 89 (e.g., braid) to ensure flexibility at the distal tip of the delivery device 10.

The elongate pusher member 30 may be formed from a flexible yet lubricious material such as polyimide, polytetrafluoroethylene (PTFE), polyetheretherketone (PEEK), fluorinated ethylene propylene (FEP), PET or the like. The elongate pusher member 30 generally has a length that permits the same to be advanced intravascularly to the site of interest. For example, the elongate pusher member 30 has a length to permit the distal end 34 to be positioned adjacent to the delivery site (e.g., aneurysm 100) while the proximal end 32 is positioned outside the patient's body. A typical range of lengths for the elongate sheath 30 may include between about 1.25 to about 2.0 meters. The elongate pusher member 30 may be formed using non-polymer materials. For example, one or more segments may be formed from metal hypotube formed from stainless steel, NITINOL, and the like.

Still referring to FIG. 1A, a retaining member 40 is located at the distal end 34 of the elongate pusher member 30. The retaining member 40 may be secured to the interior of the elongate pusher member 30 as is shown in FIGS. 1 and 4. For example, the retaining member 40 may be bonded to the elongate pusher member 30 using an adhesive, weld, solder, or the like. The retaining member 40 includes a clasp portion 42 that is used to releaseably hold the securing member 20. The clasp portion 42 includes a recess 44 and finger 46. The securing member 20, which may be in the form of a loop or hoop, is positioned around the finger 46 and is contained within the recess 44. The finger portion 46 of the retaining member 40 may include an angled surface 48 to aid in the release of the securing member 20 upon deployment. The angled surface 48 may be polished or coated with a lubricious material to enable a smooth release of the coil 14 from the retaining member 40.

Still referring to FIG. 1A, the retaining member 40 includes an aperture or lumen 50 that passes through at least a portion thereof. As seen in FIG. 1A, the aperture 60 passes through the main portion of the retaining member 40 in addition to the clasp portion 42. The aperture 50 is sized to receive the elongate releasing member 60 (discussed in more detail below). When the elongate releasing member 60 passes through the aperture 50 in the clasp portion 42, the retaining member 40 is in a closed or secured state. Conversely, when the elongate releasing member 50 is pulled proximally such that it does not pass through the aperture 50 in the clasp portion 42, the retaining member 40 is in the open position thereby permitting the coil 14 to be released from the retaining member 40 (described in more detail below). The coil joint or juncture formed between the securing member 20, clasp portion 42, and elongate releasing member 60 is an articulating joint which allows device flexibility and thus prevents microcatheter kickback.

The retaining member 40 may be made from a metallic material such as, for instance, stainless steel, NITINOL, or the like. For example, the retaining member 40 may be fashioned by laser cutting or electrical discharge machine (EDM) of a template or substrate such as metal hypotube. Alternatively, the retaining member 40 may be formed by laser cutting, EDM wire cutting or even mechanical grinding using a fine grinder. The retaining member 40 can also be integrated directly into the tip of the elongate sheath 30.

The device 10 includes an elongate releasing member 60 disposed within the lumen 36 of the elongate sheath 30. The elongate releasing member 60 has a distal end 62 and a proximal end 64. The elongate releasing member 60 is formed from a flexible yet sturdy material that provides sufficient columnar strength to avoid breakage during the deployment process. For example, the elongate releasing member 60 may be formed from one or more sires or filaments. The wire(s) may be formed from a metal or alloy such as NITINOL, titanium, stainless steel or the like. Alternatively, filament(s) may be formed from a polymer material such as polyimide, polypropylene, polyetheretherketone (PEEK), polytetrafluoroethylene (PTFE), and the like.

The elongate releasing member 60 is slidable relative to the elongate pusher member 30. For example, in one aspect, the elongate releasing member 60 can be pulled or retracted proximally relative to the elongate pusher member 30 to unsecure or unlock the clasp portion 42. In one aspect of the invention, the elongate releasing member 60 is secured relative to the elongate pusher member 30 to prevent accidental deployment of the coil 14. For example, a tight or friction fit might be formed between the distal end 64 of the elongate releasing member 60 and the proximal end 32 of the elongate pusher member 30 thereby requiring a certain threshold amount of retracting force before the elongate releasing member 60 can move relative to the pusher member 30. Alternatively, an adhesive or other bonding agent may be used to secure the proximal end 64 of the elongate releasing member 60 to the proximal end 32 of the elongate pusher member 30. The adhesive or bonding agent would, of course, break upon application of sufficient force applied to the elongate releasing member 60.

In yet another alternative embodiment, a locking member 120 such as that disclosed in FIG. 1A may be used to releasably secure the elongate releasing member 60 relative to the elongate pusher member 30. In the embodiment of FIG. 1A, the locking member 120 may be a compressible member made of a polymeric or even rubber material that includes an aperture 122 for passage of the elongate releasing member 60. The locking member 120 may include a tapered section such that as the locking member 120 is inserted into the proximal end 32 of the pusher member 30 the locking member 120 forcibly grips the elongate releasing member 60 to prevent both distal and proximal movement of the elongate releasing member 60. In this regard, the locking member 120 acts as a safety device to prevent premature deployment of the coil 14.

Figure 1B:
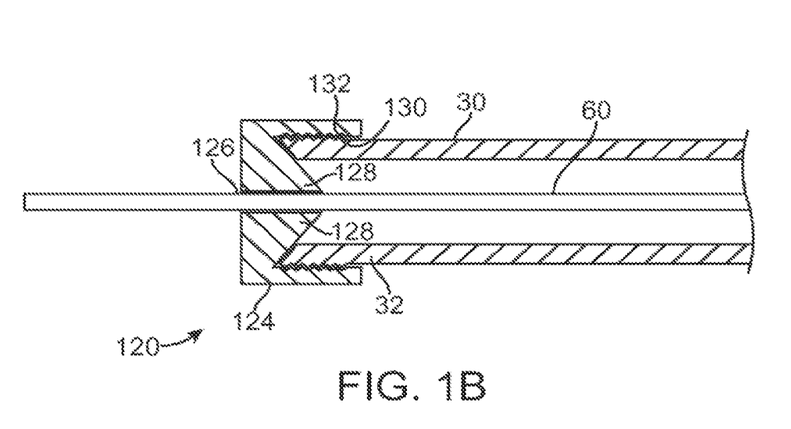
FIG. 1B is a cross-sectional view of the proximal end of a delivery device according to another embodiment.

FIG. 1B illustrates an alternative embodiment of the locking member 120. In this embodiment, the locking member 120 is a proximal cap 124 that includes an aperture 126 that allows passage of the elongate releasing member 60. In addition, the locking member includes one or more gripping members 128 that grip the elongate releasing member 60 when the cap 124 is secured to the pusher member 30. For example, the proximal end 32 of the pusher member 30 may include threads 130 that engage with corresponding grooves 132 on the interior of the cap 124. As the cap 124 is tightened down on the proximal end 32 of the pusher member 30, the one or more gripping members 128 grip the elongate releasing member 60 and thus prevents both distal and proximal movement of the elongate releasing member 60 relative to the pusher member 30.

Figure 1C:
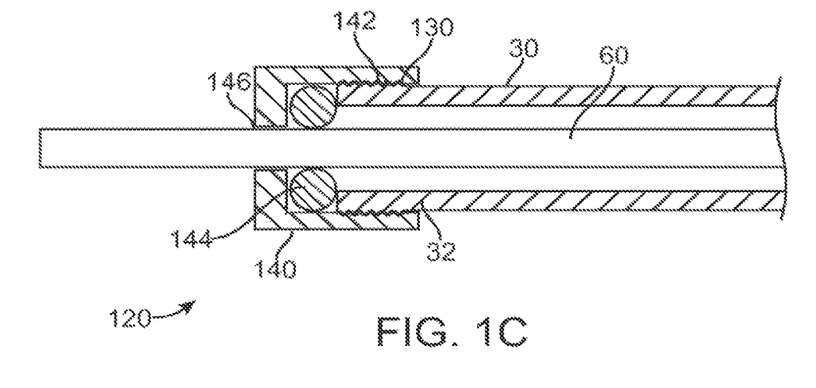
FIG. 1C is a cross-sectional view of the proximal end of a delivery device according to another embodiment.

FIG. 1C illustrates another alternative embodiment of the locking member 120. In this embodiment, the locking member 120 is a proximal end cap 140 that engages with threads 130 on the proximal end 32 of the pusher member 30 via corresponding grooves 142 or the like. In addition, a flexible or compressing O-ring 144 is disposed within the end cap 140 compresses in response to tightening of the proximal end cap 140. Specifically, the O-ring 144 expands in the radial direction and engages with the elongate releasing member 60 to lock the elongate releasing member 60 relative to the pusher member 30. The O-ring 144 may be formed from a flexible material such as rubber, NYLON, PTFE, or other polymeric material used in medical applications. The end cap 140 includes an aperture 146 through which the elongate releasing member 60 passes.

Figure 2A:
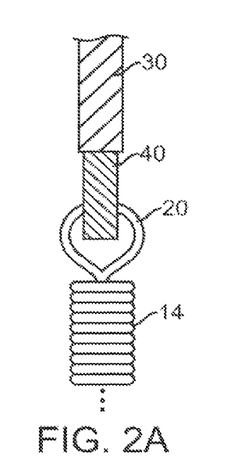
FIG. 2A is a top plan view of the distal end of the delivery device shown in FIG. 1A.
Figure 2B:
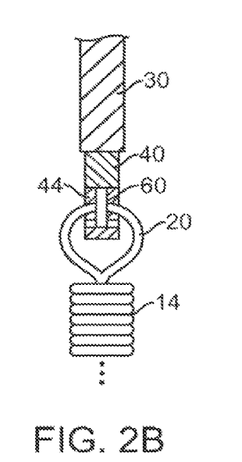
FIG. 2B is a bottom plan view of the distal end of the delivery device shown in FIG. 1A.
Figure 2C:
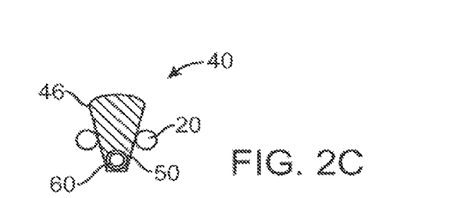
FIG. 2C is a cross-sectional view of the delivery device of FIG. 1A taken along the line A-A' according to a first embodiment.
Figure 2D:
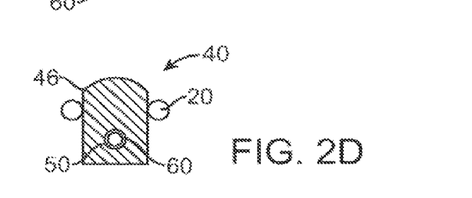
FIG. 2D is a cross-sectional view of the delivery device of FIG. 1A taken along the line A-A' according to a second embodiment.
Figure 2E:
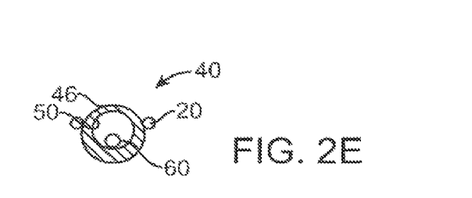
FIG. 2E is a cross-sectional view of the delivery device of FIG. 1A taken along the line A-A' according to a third embodiment.

FIGS. 2A and 2B illustrate top down and bottom up views, respectively, of the securing member 20 of a coil 14 being loaded onto the clasp portion 42 of a retaining member 40. The securing member 20 is in the form of a loop or hoop that is secured to the proximal end 18 of the coil 14. While the securing member 20 is shown as a closed loop structure in FIGS. 2A and 2B, the securing member 20 may also be formed as open structure such as a hook or the like (not shown). FIGS. 2C, 2D, and 2E illustrate three different cross-sectional views of the finger 46 taken along the line A-A' in FIG. 1A. FIG. 2C illustrates a finger 46 that is tapered or angled. This embodiment may provide for easier release of the securing member 20 from the clasp portion 42 during delivery. Of course, the finger 46 need not be tapered as is shown, for example, in FIG. 2D. FIG. 2E illustrates yet another embodiment of the finger 46 having a generally circular cross-sectional shape. The retaining member 40 is formed from stainless steel hypotube.

Figure 3A:
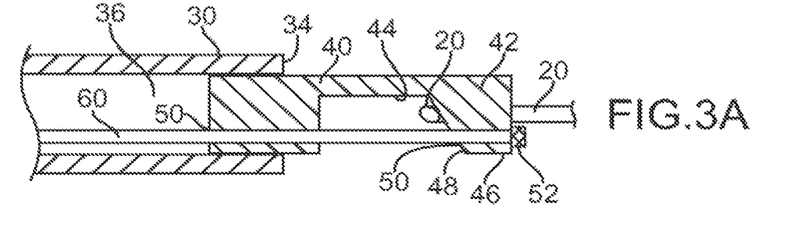
FIG. 3A is a cross-sectional view of a distal end of the delivery device according to one aspect of the device. A stop is shown on the clasp portion of the retaining member.

FIG. 3A illustrates one alternative embodiment of the device 10 wherein the retaining member 40 includes a stop 52 that is positioned at the end of the finger 46. The stop 52 prevents the elongate releasing member 60 from passing through the aperture 50. In this regard, the stop 52 acts as a safety device that prevents the elongate releasing member 60 from poking or injuring the aneurysm. The stop 52 may be formed as a cap, weld, or the like that covers at least part of the aperture 50 so as to prevent the full passage of the elongate releasing member 60 therethrough. The stop 52 may be even be formed by a constriction, narrowing, or obstruction that is present inside the aperture 50 in the finger portion 46 of the retaining member 40.

Figure 3B:
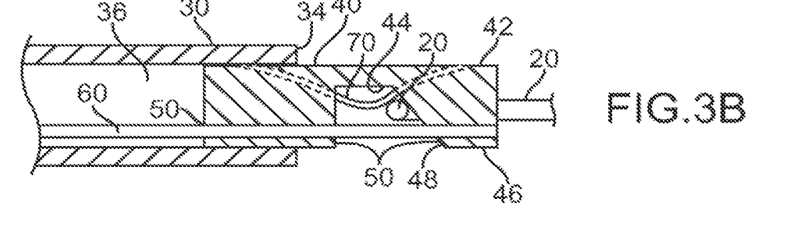
FIG. 3B is a cross-sectional view of a distal end of the delivery device according to another aspect of the device. A biasing member is formed on the clasp portion of the retaining member.

FIG. 3B illustrates another alternative embodiment of the device 10. In this embodiment, the retaining member 40 includes a biasing member 70 that is located within the recess 44 of the retaining member 40. The biasing member 70 may take the form of an elastic of flexible wire or spring that aids in releasing the securing member 20 from the finger 46. The biasing member 70 may be positioned such that natural tendency of the biasing member 70 is to push out or eject the securing member 20 from the clasp 42 of the retaining member 40. The biasing member 70 may be formed using a metal or even polymer material.

Figure 3C:
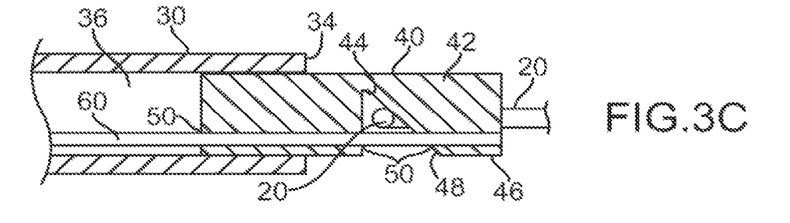
FIG. 3C is a cross-sectional view of a distal end of the delivery device according to another aspect of the device. The clasp portion of the retaining member includes an angular contact surface.

FIG. 3C illustrates still another alternative embodiment of the retaining member 40. In this embodiment, the angled surface 48 of the finger 46 has at least a portion of the surface formed to have a continuously changing slope. In this regard, the slope of the angled surface 48 may be modified so that it becomes progressively easier for the securing member 20 to slide off the finger 46. For example, the angled surface 48 may have a certain degree of convexity as is shown in FIG. 3C. In addition, the angled surface 48 may be coated with an optional low-friction or lubricious coating (not shown) to reduce frictional forces between the securing member 20 and the angled surface 48.

Figure 3D:
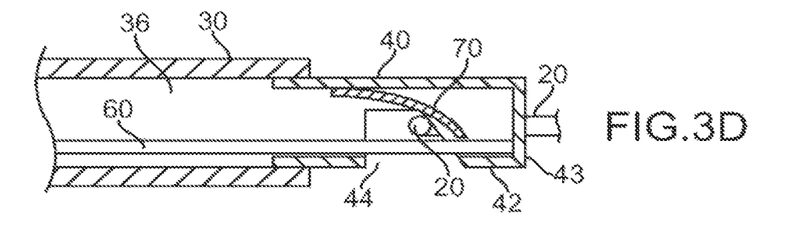
FIG. 3D is a cross-sectional view of a distal end of the delivery device according to another aspect of the device. A biasing member having one end thereof fixed is shown in the clasp portion of the retaining member.

FIG. 3D illustrates another embodiment of the retaining member 40. According to this embodiment, the clasp portion 42 of the retaining member 40 includes a distal wall 43 that prevents the elongate releasing member 60 from poking or injuring the aneurysm. In this regard, there is no need for a separate stop 52 or the like. In addition, in this embodiment a biasing member 70 is at least partially disposed inside the recess 44 of the retaining member 40. Unlike the biasing member 70 of FIG. 3B, the biasing member 70 of FIG. 3D is affixed only at one end. The biasing member 70 may be constructed of a metallic or even polymer based material. The biasing member 70 is biased in a spring-like fashion such that there is a natural force or tendency to eject the securing member 20 out of the clasp portion 42 when the releasing member tip slides out of the recess 44.

FIG. 4 illustrates an alternative embodiment of a delivery device 10. This embodiment is similar to the embodiment illustrated in FIG. 1A with the exception that a coil member 80 and stretch resistant member 89 are secured to the distal end 34 of the elongate pusher member 30. The coil member 80 may be formed from a plurality of windings 82 of wire (e.g., metallic or alloy). The coil member 80 may be flexed about the its long axis such that the delivery device 10 incorporating this feature has added flexibility. To a certain extent, the coil member 80 acts as a flexible component that advantageously reduces microcatheter recoil or kick-back. The coil member 80 is encapsulated in a stretch resistant member 89 (e.g., braid). The coil member 80 may inserted into the lumen 36 of the elongate pusher member 30 as shown in FIG. 4. In this regard, a proximal end 84 of the coil member 80 may be bonded to an interior surface o the elongate pusher member 30. The coil member 80 may be bonded using a weld, solder, adhesive, or other known technique. Alternatively, the coil member 80 and stretch resistant member 89 may abut against the distal most end 34 of the elongate pusher member 30 (not shown). A surrounding jacket or sheath may be used to secure the coil member 80 and stretch resistant member 89 to the elongate pusher member 30.

Still referring to FIG. 4, the distal end 86 of the coil member 80 and stretch resistant member 89 are secured to the retaining member 40. The distal most end 86 may be bonded directly to the retaining member via a weld, solder, adhesive, or the like. Alternatively, the retaining member 40 may pass through a portion of the lumen formed inside the coil member 80 and stretch resistant member 89. The retaining member 40 can then be secured to an interior surface of the coil member 80. A stretch resistant member 89 in the form of a tubular sheath or jacket may surround the coil member 80 and a portion of the retaining member 40. The stretch resistant member may be formed as a braided structure about the periphery of the coil member 80. FIG. 4 also illustrates the use of a stop 52 to prevent distal advancement of the elongate releasing member 60. The use of the stop 52 is, however, optional.

FIG. 5 illustrates a process of delivering the coil 14 to an aneurysm 100 in a blood vessel 110. As seen in FIG. 5, a catheter 90 device such as a microcatheter is positioned within the vessel 110 so as to place the distal tip adjacent to the entry point or neck of the aneurysm 100. The device 10 of the type described herein is then advanced through the catheter 90. The device 10 is advanced to place the coil 14 located at the distal end of the elongate pusher member 30 in the aneurysm 100. One or more radiopaque markers (not shown) located on the catheter 90 and elongate pusher member 30 or the elongate releasing member 60 may be used to aid the physician in positioning the device 10 for deployment of the coil 14.

Figure 6A:
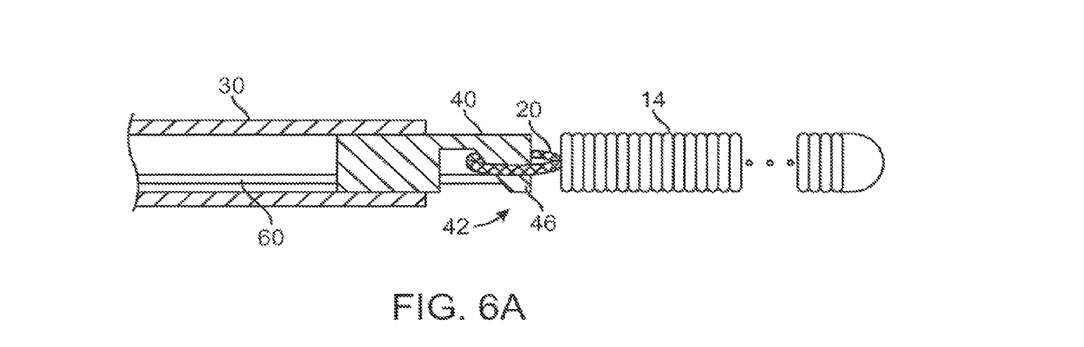
FIG. 6A is a partial cross-sectional view of the distal end of a delivery device of the type illustrated in FIG. 1A. A vaso-occlusive coil is shown being secured to a retaining member.
Figure 6B:
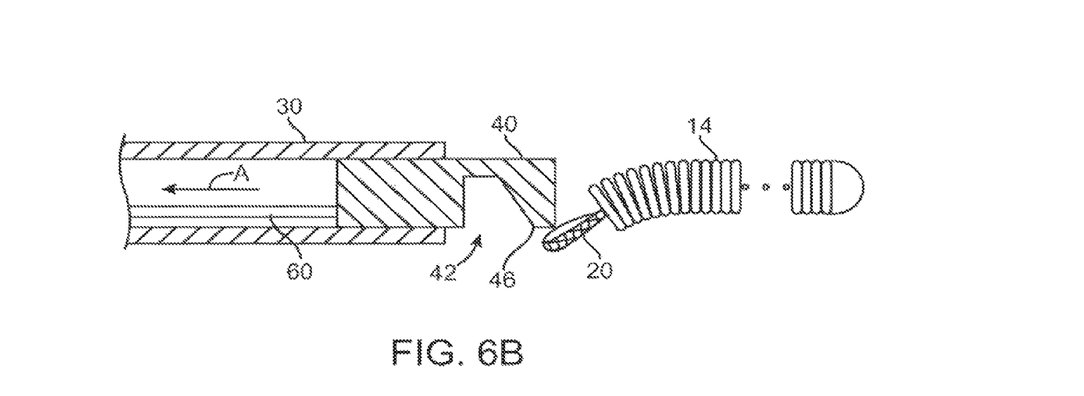
FIG. 6B is a partial cross-sectional view of the distal end of the delivery device illustrated in FIG. 6A. The elongate releasing member is retracted proximally in the direction of the arrow to open the clasp region of the retaining member. The vaso-occlusive coil is then released from the retaining member.

FIGS. 6A and 6B illustrates the process of loading and releasing a coil 14 using the delivery device 10. FIG. 6A illustrates the clasp 42 in the closed state, namely, the elongate releasing member 60 is disposed inside the aperture 50 of the retaining member 40. The securing member 20 of the coil 14 is thus prevented from being released from the finger 46 of the releasing member 40.

The coil 14 may be loaded onto the retaining member 40 by first opening the clasp portion 42 (if not already in the open state). The clasp 42 is opened by pulling the elongate releasing member 60 proximally to create an opening to the recess 44. Alternatively, the elongate releasing member 60 is entirely absent from the device 10 at this point and is advanced distally in a later step. The finger 46 of the retaining member 40 can then be inserted into the securing member 20 on the coil 14. The securing member 20 thus wraps around the finger 46 as best seen in FIGS. 1 and 2A. The elongate releasing member 60 can then be advanced distally such that the distal end 62 passes through the aperture 50 in the retaining member 40. Distal advancement may be stopped because of an optional stop 52. Alternatively, one or more markings on the elongate releasing member 60 or elongate pusher member 30 may indicate that the secured (e.g., locked) state has been reached. In still another aspect, the length of the elongate releasing member 60 extending proximally with respect to the elongate pusher member 30 may indicate that a locking state has been reached.

In one aspect of the invention, the elongate releasing member 60 is secured to the proximal end 32 of the elongate pusher member 30 after loading the coil 14 on the retaining member 40. Locking of the elongate releasing member 60 may be accomplished by using an adhesive or other bonding agent between the proximal end 32 of the elongate pusher member 30 and the elongate releasing member 60. Alternatively, a locking member 122 such as a proximal cap (FIGS. 1A, 1B, 1C, and 4) located on the proximal end 32 of the elongate pusher member 30 may fixedly secure the elongate releasing member 60 relative to the elongate pusher member 30. The locking state between the elongate releasing member 60 and the elongate pusher member 30 may be opened by opening or releasing the locking member 120 so that the elongate releasing member 60 can be moved relative to the elongate pusher member 30 to release the coil 14. For example, a mechanical lock (e.g., cap 122) may be twisted, unscrewed or otherwise removed or unloosened to permit movement between the elongate pusher member 30 and the elongate releasing member 60.

In contrast, FIG. 6B illustrates the clasp 42 in an open configuration with the securing member 20 being released from the finger 46 of the releasing member 40. The clasp 42 is opened by retracting or pulling the elongate releasing member 60 proximally in the direction of arrow A. For example, the elongate pusher member 30 may be held stationary while the physician grasps the proximal end 64 of the elongate releasing member 60 and pulls the same proximally.

As shown in FIG. 6B, the coil 14 may naturally release from the clasp 42 as after the elongate releasing member 60 is pulled proximally. As explained above, a biasing member 70 of the type disclosed in FIG. 3B may optionally be used to assist in releasing the securing member 20 from the finger 46 of the retaining member 40.

Once the coil 14 is released from the delivery device 10, the elongate pusher member 30 and elongate releasing member 60 may then be retrieved from the body by withdrawing the elongate pusher member 30 together with the elongate releasing member 60 in the proximal direction. If additional coils 14 need to be deployed, then another delivery device 10 with a coupled coil 14 may be advanced through the catheter 90 as described above. After all the coil(s) 14 have been deployed, the catheter 90 is then withdrawn from the vessel 110.

One advantage of the delivery device 10 described herein is that a pull-to-release process is used to deploy the coil 14. Because a pulling motion is used, there is no risk of poking or puncturing the aneurysm 100 that is inherent in push-based delivery devices. In this regard, the detachment of the coil 14 from the retaining member 40 is atraumatic. In addition, because the coupling between the coil 14 and the elongate releasing member 50 is mechanical, detachment is faster than electrolytic-based delivery devices. Finally, the nature of articulating coupling between the coil 14 and the pusher tip provides a flexible joint and thus reduces catheter kick-back during the embolization coiling procedure.

While embodiments of the present invention have been shown and described, various modifications may be made without departing from the scope of the present invention. The invention, therefore, should not be limited, except to the following claims, and their equivalents.

What is claimed is:

1. A system, comprising:
   an elongate pusher member having a distal end and a proximal end and a lumen extending between the distal and proximal ends;
   an elongate filament having a distal end and a proximal end, the elongate filament being slidable within the lumen of the elongate pusher member;
   a clasp disposed on the distal end of the elongate pusher member, the clasp having a recess, an angled surface within the recess, and an aperture sized to receive the distal end of the elongate filament; and
   an occlusive element including a loop positioned at a proximal end of the occlusive element, wherein the loop is secured to the clasp and bears upon the angled surface within the recess when the elongate filament is disposed in the aperture of the clasp, and is unsecured and slides along the angled surface to exit the recess when the elongate filament is retracted proximally from the aperture of the clasp.

2. The system of claim 1, wherein the angled surface is coated with a polymer.

3. The system of claim 1, further comprising a stop on the clasp, the stop limiting movement of the elongate filament through the aperture in the clasp.

4. The system of claim 1, the clasp further including a biasing member.

5. The system of claim 4, wherein the biasing member comprises a spring.

6. The system of claim 1, wherein the clasp is formed from hypotube.

7. The system of claim 1, wherein the elongate filament comprises a wire.

8. The system of claim 1, wherein the clasp is bonded to the interior of the elongate pusher member.

9. The system of claim 1, wherein the occlusive element comprises a coil, and the loop is a proximal winding of the coil.

10. A system, comprising:
    an elongate pusher member having a distal end and a proximal end and a lumen extending between the distal and proximal ends;
    a coil member secured to the distal end of the elongate pusher member;
    an elongate filament having a distal end and a proximal end, the elongate filament being slidable within the lumen of the elongate pusher member and coil member;
    a clasp disposed on the distal end of the coil member, the clasp having a recess, an angled surface within the recess, and an aperture sized to receive the distal end of the elongate filament; and
    an occlusive element including a loop positioned at a proximal end of the occlusive element, wherein the loop is releasably secured to the clasp and bears upon the angled surface within the recess when the elongate filament is disposed in the aperture of the clasp and is unsecured when the elongate filament is retracted proximally from the aperture of the clasp.

11. The system of claim 10, further comprising a stop on the clasp, the stop limiting movement of the elongate filament through the aperture in the clasp.

12. The system of claim 10, the clasp further including a biasing member.

13. The system of claim 12, wherein the biasing member comprises a spring.

14. The system of claim 10, wherein the coil member comprises a stretch resistant member.

15. The system of claim 14, wherein the clasp is bonded to both the interior of the distal end of the coil member and the stretch resistant member.

16. The system of claim 10, wherein occlusive element comprises a coil, and the loop is formed from a proximal winding of the coil.

* * * * *

UNITED STATES PATENT AND TRADEMARK OFFICE
CERTIFICATE OF CORRECTION

| | | |
|---|---|---|
| PATENT NO. | : 9,486,223 B2 | Page 1 of 1 |
| APPLICATION NO. | : 14/589642 | |
| DATED | : November 8, 2016 | |
| INVENTOR(S) | : Like Que et al. | |

It is certified that error appears in the above-identified patent and that said Letters Patent is hereby corrected as shown below:

On the Title Page

Item (54) and in the Specification, Column one please correct the title to reflect the following:
-- MECHANICALLY DETACHABLE VASO-OCCLUSIVE DEVICE --

Signed and Sealed this
Twenty-seventh Day of June, 2017

Joseph Matal
*Performing the Functions and Duties of the*
*Under Secretary of Commerce for Intellectual Property and*
*Director of the United States Patent and Trademark Office*